(12) United States Patent
Kristiansen

(10) Patent No.: US 8,398,553 B2
(45) Date of Patent: Mar. 19, 2013

(54) METHOD AND AN APPARATUS FOR RECORDING BLADDER VOLUME

(75) Inventor: Niels Kristian Kristiansen, Viby J (DK)

(73) Assignee: Urodan ApS, Aarhus N (DK)

( * ) Notice: Subject to any disclaimer, the term of this patent is extended or adjusted under 35 U.S.C. 154(b) by 1074 days.

(21) Appl. No.: 11/621,748

(22) Filed: Jan. 10, 2007

(65) Prior Publication Data

US 2007/0167768 A1    Jul. 19, 2007

Related U.S. Application Data

(63) Continuation-in-part of application No. 10/477,351, filed as application No. PCT/DK02/00320 on May 16, 2002, now abandoned.

(51) Int. Cl.
*A61B 8/00* (2006.01)

(52) U.S. Cl. ........ 600/449; 600/407; 600/437; 600/438; 600/443

(58) Field of Classification Search .................. 600/407, 600/437, 438, 443, 449
See application file for complete search history.

(56) References Cited

U.S. PATENT DOCUMENTS

| | | | |
|---|---|---|---|
| 3,881,164 A | 4/1975 | Kossoff | 340/1 R |
| 4,074,564 A | 2/1978 | Anderson | 73/596 |
| 4,219,846 A | 8/1980 | Auphan | 358/112 |
| 4,307,613 A | 12/1981 | Fox | 73/626 |
| 4,917,097 A | 4/1990 | Proudian et al. | 128/662.06 |
| 4,926,871 A | 5/1990 | Ganguly et al. | 128/660.07 |
| 5,058,591 A | 10/1991 | Companion et al. | 128/661.03 |
| 5,235,985 A | 8/1993 | McMorrow et al. | 128/660.07 |
| 5,331,548 A * | 7/1994 | Rollema et al. | 600/561 |
| 5,699,805 A | 12/1997 | Seward et al. | 128/662.06 |
| 5,871,019 A | 2/1999 | Belohlavek | 128/916 |
| 5,964,710 A | 10/1999 | Ganguly et al. | 600/449 |
| 6,359,190 B1 | 3/2002 | Ter-Ovanesyan et al. | 604/361 |

* cited by examiner

*Primary Examiner* — Tse Chen
*Assistant Examiner* — Mark Remaly
(74) *Attorney, Agent, or Firm* — Winston & Strawn LLP

(57) ABSTRACT

A non-invasive method and apparatus for monitoring the bladder volume in humans or animals. The monitoring measurements are based on the analysis of ultrasound signals from at least two individual ultrasound transducer arrays. Each one individual ultrasound transducer array has a contact face, which is arranged in order to transmit an ultrasonic signal through an abdominal surface of an individual being monitored. The method and apparatus includes the arranging of each individual transducer array on the abdominal surface around an axis which extends from a point on the abdominal surface through a point on or within the urinary bladder. The method and apparatus further comprises that each individual transducer array is arranged to scan the bladder using a two-dimensional scan plane which extends radially from the transducer array through the bladder.

28 Claims, 5 Drawing Sheets

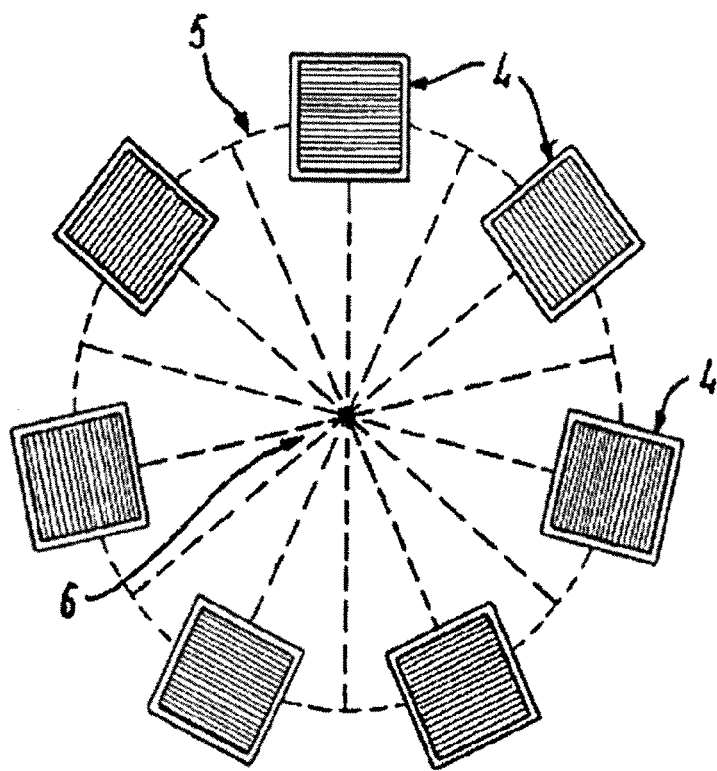
FIG. 2
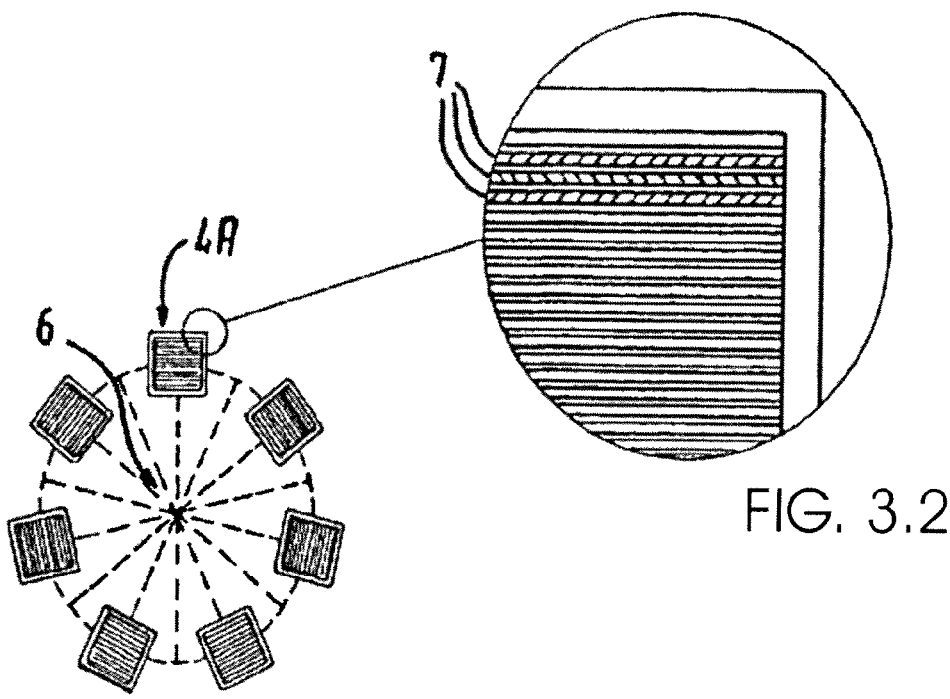
FIG. 3.2
FIG. 3.1

METHOD AND AN APPARATUS FOR RECORDING BLADDER VOLUME

CROSS-REFERENCE TO RELATED APPLICATIONS

This application is a continuation-in-part of application Ser. No. 10/477,351 filed Jan. 9, 2004 now abandoned as the U.S. National State application under 35 U.S.C. 371 of International Application no. PCT/DK02/00320 filed May 16, 2002, the entire content of each of which is expressly incorporated herein by reference thereto.

FIELD OF THE INVENTION

The invention relates to a non-invasive method and apparatus for monitoring the bladder volume in humans or animals.

BACKGROUND OF THE INVENTION

The human or mammal urinary bladder is a triangularly shaped, hollow organ, located in the lower abdomen. The bladder walls are elastic, and can expand to hold the urine excreted from the kidneys and contract in order to empty the urine through the urethra. There are a number of disorders or ailments that can affect the urinary system, which could require the continuous monitoring of the bladder, long or short term, for diagnostic and/or treatment purposes, in both research and clinical connection.

Another great need for long term monitoring of the volume of the bladder with a user-friendly easily portable apparatus is found in patients who suffer from involuntary nocturnal incontinence. For example is urinary nocturnal incontinence a problem for up to 15% of all children aged 3-10 years.

DESCRIPTION OF THE PRIOR ART

The techniques used till now for determining the volume of the bladder in humans or animals comprise the generally known image diagnostic techniques based on e.g. magnetic resonance (MR), X-ray, nuclear medicine or ultrasound, where it is characteristic for some of these techniques that they call for the use of heavy and large equipment, which normally requires that the patient is confined to bed during the measurement.

Ultrasound equipment is available which can measure the volume of the bladder in ambulatory patients. This equipment is based on the use of a single ultrasound transducer, which rotates the transducer over the patient's bladder mechanically by means of a gear system driven by an electric motor, such that the entire bladder is scanned, and then, via signal processing in a computer, a three-dimensional (3D) reconstruction of the surface of the bladder and thereby also the volume of the bladder may be created.

The ultrasound measuring equipment driven by an electric motor is portable in the sense that the equipment is fixed in a belt, which is tightened around the patient on whom measurements are to be performed. The system, however, is relatively large and heavy because of the mechanical components used for the rotation of the ultrasound transducer and therefore not comfortable for the patients to wear. Also, the bulky structure with the complicated, mechanical movements means that the apparatus will inevitably generate mechanical noise which may also be unpleasant to the patient. The mechanically complicated structure will moreover be vulnerable to external impacts, which may occur if the unit is e.g. dropped. The complicated structure will also be expensive to manufacture and require relatively great current maintenance costs.

Thus, it is a problem of the above mentioned techniques that they cannot be used in practice for long term monitoring of ambulatory patients, which is a great clinical need, e.g. in connection with the evaluation of the effect of recently developed medicine.

If these individuals could be equipped with a small, simple and non-hampering measuring device, which could measure the volume of the bladder continuously and emit a signal when the bladder reached a preselected maximum volume, the individuals would have an alarm that woke them before the urinary incontinence was initiated, so that the individuals could urinate in time and thereby avoid the inconvenience of the otherwise occurring urinary incontinence.

Within the scope of the present invention, the references to the front and back wall of the bladder, the front wall means the urinary bladder wall which is closest to the abdominal surface, while the back wall means the urinary bladder wall which is distal from the abdominal surface. The reference to a side wall of the bladder, is interpreted as any part of the bladder wall that stretches from the front wall to the back wall.

U.S. Pat. No. 5,235,985 discloses an apparatus, which automatically determines the volume of urine in a human bladder. This apparatus uses one ultrasound transducer, comprised of a plurality of individual ultrasound transducer elements. The apparatus uses a collection of transducer elements arranged in a pre-selected pattern as transmission antennas, and another collection of transducer elements arranged in a pre-selected pattern as receiving antennas. The transmission and receiving antennas make use of dedicated and separate transducer elements, used as either transmission or receiving elements.

By using separate and dedicated transducer elements for the transmission and reception of ultrasound signals the number of transducer elements in a single transducer array is increased significantly compared to a transducer array that uses the same transducer elements for transmission and reception.

One method of transmission and receipt, according to U.S. Pat. No. 5,235,985, allows the scanning of the bladder in different one-dimensional scan planes at different angles relative to each other. These scan planes intersect each other at the center of each scan plane, and produce a fan like structure of scan planes, which protrudes from the center of the transmission antennas. The method described in U.S. Pat. No. 5,235,985 is called an annular ultrasonic transmission method.

When an object is scanned using two-dimensional scan planes, the optimal echo is received from structures, which are perpendicular or close to perpendicular, to the transmission beam. When the transmission source is placed above the center of the bladder, the front and back walls of the bladder can easily be detected using one single source, while the side walls, which may be close to parallel to the source, do not backscatter the sound waves optimally.

As the apparatus suggested in U.S. Pat. No. 5,235,985, has one single two-dimensional transducer array, the focus point of all the ultrasonic scan planes is positioned at the center of the transmission antenna and all scan planes produced by the transmission antenna easily detect the front and back wall of the bladder, while the side walls are largely undetected. This means that the bladder volume calculations are primarily based on measurements on the front and back walls of the bladder.

U.S. Pat. No. 5,964,710 discloses another system for estimating the volume of fluid in the bladder. This system also uses a plurality of ultrasound transducer elements, arranged in one single two-dimensional array, to scan the bladder using a plurality of scan planes, which are transmitted in a fanlike structure from the two-dimensional array and the scan planes do not intersect each other. This system suffers from similar deficiencies as the above-mentioned apparatus, as the transducer elements are mounted in a single transducer, which means that the source of all scan planes originate in the transducer. This would mean that the transducer easily detects the front and back wall of the bladder, while the side walls go largely undetected, and calculations of the bladder volume would be based on measurements on the front and back walls of the bladder.

As the urinary bladder is an elastic non-symmetrical organ, which can be deformed by posture or by the quantity of urine contained in the bladder, the above mentioned measurement techniques may be prone to measure incorrectly as the measurements are based on front and back wall detection and the outlines of the bladder are estimated using these measurements. Therefore, is there a need for a ultrasound bladder measurement system which is able to measure the size of the bladder, i.e. the volume of urine in the bladder, based on not only front and back wall measurements, but side wall measurements as well.

SUMMARY OF THE INVENTION

The present invention now enables continuous monitoring of the volume of the bladder in humans or animals who or which move about free and easy or are at sleep. These continuous monitoring measurements of the bladder in humans or animals may be based on other areas of the bladder than the front and back wall. Also, these measurements are intended to increase the accuracy of the monitoring measurements of the bladder in humans or animals, as a means to minimize the likelihood of false measurements. The invention also provides an apparatus for monitoring the bladder volume which may be concealed from public view, on the body of the individual being monitored.

Within the scope of the present invention, the reference to an individual ultrasound transducer array should be understood as a stand-alone array of ultrasound transducer elements combined into a single unit, where the transducer array can transmit and receive ultrasound signals.

The novel and unique way in which the present invention fulfills the abovementioned objects, is by presenting a method where the monitoring measurement is based on the analysis of signals from at least two individual ultrasound transducer arrays, having a contact face, which are arranged to transmit an ultrasonic signal through an abdominal surface of an individual being monitored, where the method comprises the arrangement of each individual transducer array on the abdominal surface around an axis which extends from a point on the abdominal surface through a point on or within the urinary bladder, and where each individual transducer array is arranged to scan the bladder using a two-dimensional scan plane which extends radially from the transducer array through the bladder.

By continuously scanning the bladder using at least two scan planes which originate away from the said axis it is possible to monitor the movement of at least two different sections of the bladder. As the quality of received ultrasound signals is optimal for transitional areas that are perpendicular to the line of travel for the ultrasound signals, the placement of the transducer arrays away from the said axis ensures that the each scan plane does not include the same bladder surface area as the at least one other scan plane. This means that the monitoring measurements are not only based on front and back wall measurements, but side wall measurements as well.

By sectioning the bladder into a plurality of scan planes, it may be assumed that if the scan planes are angled randomly with respect to the bladder, the measurements would not consistently represent the true size of the bladder, for instance if one scan plane sections a small part of a side wall. Therefore it is important to ensure that the at least two scan planes complement each other, which may be accomplished by arranging each two-dimensional scan plane to be substantially in parallel to said axis and to intersect the said axis. This means that each individual scan plane intersects at least one other individual scan plane in the said axis.

The optimal reception of a ultrasound signal by a ultrasound transducer array is when the contact face of the transducer array is perpendicular to the travel path of the ultrasound signal. By arranging the at least two individual transducer arrays around the said axis on the abdominal surface, the transducer array contact face would not be positioned perpendicular to the bladder, which means that the reception of the ultrasound signals would not be optimal. Therefore, a surface normal of the transducer array contact face may be arranged to converge towards the said axis, thus optimizing the reception of the ultrasound signal by the transducer array.

The size of a bladder is optimally measured by measuring the distance between the walls of the largest section of the bladder. In order to maximize the possibility that the at least two individual scan planes will measure the largest sections of the bladder, the point on or within the urinary bladder where the said axis extends through may be arranged to be positioned at the mass center of the bladder.

The individual transducer arrays scan the bladder using a two-dimensional ultrasound scan plane, which is transmitted through the abdominal surface towards the bladder. One method of producing a two-dimensional scan plane is by arranging the individual transducer array as a one-dimensional transducer array of the phased-array kind. The phased-array transducer array does not contain mechanically moveable components, but is composed of several ultrasound elements, typically of piezoelectric crystals, arranged in parallel. Thus, without mechanically movable parts, a phased-array ultrasound transducer may perform scanning in a plane, in the longitudinal direction, in which the piezoelectric crystals are arranged, by individual excitation of the individual crystals with a time delay between each excitation.

As the monitoring measurements are performed using at least two individual transducer arrays, the individual transducer arrays may be arranged to be substantially positioned equidistantly on the abdominal surface around the said axis in the form of a closed curve selected from the group comprising a circle, an ellipse or a n-sided polygon.

Within the scope of the present invention, the reference to the angle between transducer arrays is understood as the angle between the scan planes produced by the transducer arrays on a circular arch, which is centered on the said axis.

In a preferred embodiment of the present invention, seven individual transducer arrays are arranged around the said axis in the form of a drawing of a circle. In order to arrange the transducer arrays equidistantly along the circle, the angle between each transducer array may be set between 45°-55°, more specifically between 50°-53°, and even more specifically close to 51, 5°, which is approximately one seventh of a full circle (360°).

In a simple embodiment of a method according to the present invention, two individual transducer arrays may be arranged as two points on a line, which intersects the said axis. As the number of transducer arrays is two, the angle between the individual transducer arrays is approximately 180° which means that the two transducer arrays are at a straight angle, or more specifically on a line. Another representation of the same arrangement could be that two individual transducer arrays are positioned around the said axis in the form of a drawing of a circle.

In an alternative embodiment of a method according to the present invention, two individual transducer arrays are arranged as two points on a line, where the two individual transducers arranged in such a way that the two scan planes are not parallel to each other, and intersect each other in the said axis. This means that the two individual transducer arrays are not distributed equidistantly around the circle, and will have an angle that is less than 180° and a preferred angle between the transducer arrays may be approximately 90°.

This means, in general, that the transducer arrays are arranged, in such a manner that the scan planes of the transducer arrays, which are the region in which the ultrasound signals are emitted and detected after reflection from transitions between tissue layers of different density, cover the bladder of the individual.

In a method which ensures that the monitoring measurements for the at least two individual transducer arrays are not receiving ultrasound reflections from the same areas of the bladder, i.e. the front and back wall, the said closed curve may advantageously be arranged to define an area of a size corresponding to at least the largest section of an empty urinary bladder. By ensuring that each transducer is positioned away from the said axis, the sectional areas of the bladder that are perpendicular to the ultrasound transmission are different for each transducer array.

In a preferred embodiment of the present invention, the said closed curve is arranged to have an area of a size of a full urinary bladder, thus ensuring that each individual transducer array is receiving optimal ultrasound reflections from different side wall areas of the bladder.

In one embodiment of the present invention, the operational sequence of each individual transducer array is determined such that the at least two individual transducer arrays may be arranged to operate one at a time. The operation of each individual transducer array one at a time may allow for the reduction of active individual transducer arrays, down to the transducer arrays that best reflect the size of the bladder. If one individual transducer array does not correlate well to the true size of the bladder, it is possible to turn of that individual transducer array, and utilize the measurements of those transducer arrays that correlate correctly with the true size of the bladder.

In a preferred embodiment of the present invention the at least two individual transducer arrays may be arranged to be operated in a random order. Since the operational order of the at least two individual transducer arrays is randomized, it allows for the possibility of switching one individual transducer array with another, or altogether removing the one individual transducer array without having to stop the monitoring measurement.

In another embodiment of the present invention, the at least two individual transducer arrays may be arranged to be operated sequentially along the path of the said closed curve. By operating the individual transducer arrays sequentially, it may be assured that the at least two individual transducer arrays contribute to the monitoring measurements, if necessary.

In order to ensure that the individual being monitored may be able to function normally in a number of different day-to-day situations without having to worry about involuntary urine leaks or discharge, the individual transducer arrays may be fixed in place on a portable fixture, which may be attached to the individual being monitored. The portable fixture is a fixture that allows for the individual transducer arrays to be held in place, on the abdominal surface, around the said axis, where the portable fixture may be arranged to be a strap, a belt, a girdle or a trouser waistband.

The at least two individual transducer arrays may be arranged to be fixed in place on the abdominal surface by adhesive means. In one embodiment of the present invention the adhesive means may be an adhesive dressing, which firstly adheres to the side walls of the individual transducer array housing and secondly to the abdominal surface of the individual being measured. This dressing encircles the contact face of the individual transducer array, and ensures that there are none unwanted coverings on the said contact face which can block the ultrasonic transmission from the contact surface through the abdominal surface. In a preferred embodiment of the present invention the adhesive means may be a ultrasonic gel pad, e.g. the gel pad described in U.S. Pat. No. 5,782,767, where the gel pad may be adhesively fastened to the abdominal surface using side flaps, welded to the gel pad. The gel pad comprises two surface areas, where one surface area of the gel pad is in contact with the abdominal surface and the other surface area is in contact with the contact face of the individual transducer array.

As mentioned, the invention also relates to a non-invasive apparatus for monitoring the bladder volume. The apparatus is characterized in that the monitoring apparatus comprises at least two individual ultrasound transducer arrays, having a contact face, and arranged in a pattern on an abdominal surface of an individual being monitored, around an axis which extend from a point on the abdominal surface through a point on or within the urinary bladder, and means for scanning the bladder using a two-dimensional scan plane which extends radially from each individual transducer array through the bladder.

Since the apparatus uses at least two individual transducer arrays, the apparatus is capable of detecting the walls of the bladder from at least two different positions, as the individual transducer arrays are placed around the said axis. The wall detection from different positions increases the accuracy of the monitoring measurements, compared to measurements that are taken from the same position.

The urinary bladder may be considered to be of a substantially a triangular shape, with a funnel like structure at the bottom, where the urinary bladder connects to the urethra. This means that scan planes transmitted from a single transmission position, focal point, would not represent the true shape of the bladder, as some side walls of the bladder would not be detected and the monitoring measurements. To further ensure that the apparatus is capable of detecting bladder walls at different positions and angles the at least two individual ultrasound transducer arrays may be mounted such that each two-dimensional scan plane generated is substantially in parallel to said axis and intersects the said axis.

In a preferred embodiment of the present invention, the said at least two individual transducer arrays may be one-dimensional transducer arrays of the phased-array kind. Each signal sweep of the phased-array transducer arrays may be timed such that each transducer element transmits a signal at a predefined point in time, which allows the focusing of the signals to a single point. By focusing the ultrasound signals that are produced by the individual transducer array, a two-dimensional scan plane can be constructed.

In a simple preferred embodiment of the apparatus according to the present invention the apparatus has two individual transducer arrays, where the two individual transducer arrays are positioned on the abdominal surface around the said axis at a 90° angle. By positioning the two ultrasound transducers at a 90° angle, the individual transducer arrays scan planes positioned perpendicular to each other, which ensures that the monitoring measurements receive sufficient data for the 3D assessment of the bladder size.

In a preferred embodiment of the apparatus according to the present invention the apparatus has at least three individual transducer arrays, where the at least three individual transducer arrays are positioned substantially equidistantly on the abdominal surface around the said axis in a pattern, in the form of a closed curve selected from the group comprising a circle, an ellipse or a n sided polygon. The at least three individual transducer arrays positioned on the closed curve, ensures that the monitoring measurements are obtained from different areas of the bladder walls which, in turn increases the likelihood that the apparatus measures the true size of the bladder and the patient can empty the bladder before any involuntary urinary leakage occurs.

The at least three individual transducer arrays can be placed around the said axis in a pattern of a closed curve, where the closed curve surrounds the said axis. In one embodiment of the present invention, the at least three individual transducer arrays can advantageously be positioned equidistantly along the drawing of a circle, where the center of the circle intersects the said axis.

The apparatus according to the present invention is capable of making monitoring measurements from different positions on the abdominal surface and not from only a single position. This may be achieved by adjusting the dimension of the said closed curve for it to define an area of the size corresponding to at least the largest section of an empty urinary bladder. Since the individual transducer arrays are placed on the said closed curve, the dimensions of the said closed curve defines the distance from the said axis to each of the individual transducer array. If the distance from the axis to each individual transducer array would be smaller than the area of the size corresponding to at least the largest section of an empty urinary bladder, the individual transducer arrays scan planes would essentially measure the portions of the bladder walls, i.e. the front and back wall of the bladder.

In a preferred embodiment of the apparatus according to the present invention the at least two individual transducer arrays may be mounted such that a surface normal of the said contact face converges towards the said axis, i.e. the said contact face is pointed towards the bladder. By pointing the contact face towards the bladder, the reception conditions for the reflected ultrasound signals is optimized as the contact face is substantially perpendicular to the surfaces which reflect the ultrasound signals.

The apparatus is intended for monitoring measurements of the size of the bladder, thus is it important for the accuracy of the monitoring measurements that the two-dimensional scan planes detect the bladder walls in areas where the bladder walls are representative to the true size of the bladder. If a two dimensional scan plane monitors a portion of the bladder where the bladder walls expand minimally as a consequence to increased quantity of urine, the monitoring measurement would not be representative of the true size of the bladder. In order to ensure that the at least two scan planes measure bladder walls that are representative to the true size of the bladder, the said point on or within the bladder may be positioned at the mass center of the bladder. This will ensure that the two dimensional scan planes will always monitor a section of the bladder that expands with increased quantity of urine in the bladder.

In a simple embodiment of the apparatus according to the present invention, the at least two individual transducer arrays may be operated one at a time. This configuration allows for the apparatus to be operated such that a minimal number of individual transducer arrays may be used for monitoring measurements, in order to conserve energy.

In an alternative embodiment of the apparatus according to the present invention, the at least two individual transducer arrays may be operated sequentially along the path of the said closed curve. The sequential operation of the individual transducer arrays, ensures that monitoring measurements are recorded from every single individual transducer array, which reduces the probability of a false assessment of the bladder size.

In yet another alternative embodiment of the apparatus according to the present invention, the at least two individual transducer arrays may be operated in a random order. As the at least two individual transducer arrays may be operated in a random order, it supports the earlier mentioned feature, where individual transducer arrays may be turned off in order to conserve energy or where individual transducer arrays may even be removed from the apparatus to minimize the weight or the physical dimensions of the apparatus, without having to reconfigure the apparatus.

In a preferred embodiment of the apparatus according to the present invention the apparatus is constructed such that a portable fixture may hold the at least two individual transducer arrays in place on the abdominal surface of the individual being monitored. Using a portable fixture the at least two individual transducer arrays may be held in place while the individual being monitored is performing daily activities without having to worry about the urinary quantity of the bladder or urinal leakage due to excessive urine in the bladder.

The portable fixture may advantageously be a fixture that allows the individual being monitored to conceal the apparatus from the public view. This could assist the individual in managing the psychological aspects of the medical condition that requires the use of the apparatus, such as the embarrassment of not being able to control ones urination. For this purpose, the portable fixture may be selected from the group of a waist strap, a belt, a girdle or a trouser waistband.

In an alternative embodiment of the apparatus of the present invention the at least two individual transducer arrays are held in place on the abdominal surface, of the individual being monitored, using adhesive means. This means that the at least two individual transducer arrays will be held in a stable position, where movement or minor contact will not displace the individual transducer arrays, as could be the case with the portable fixture.

The concealment of the apparatus and operational simplicity are important aspects of the present invention. Thus, it is important that the apparatus does not have any bulky external components, as well as all the necessary means for normal monitoring purposes are integrated into the said portable fixture. Therefore, the said portable fixture may have an integrated controller, which has electronic circuits, at least one microprocessor, memory storage and means for controlling the ultrasound signal transmission of the at least two individual transducer arrays, processing the ultrasound signals received by the at least two individual transducer arrays, registering the monitoring measurements and providing alarming means for alarming the individual being monitored, by audio means, mechanical means, such as vibration, and/or transferring an wireless alarm signal to an external unit. It may be taken for granted that the apparatus is battery operated.

When referring to the means for controlling the ultrasound signal transmission and reception, it may be understood as the method and electrical components for exciting the individual transducer elements, determining the frequency of excitation, setting time delays and the reception of the reflected ultrasound signals. These methods and electrical components are known to those skilled in the art.

At the time where the apparatus is taken into use and is fixed on the abdominal surface of an individual to be monitored the apparatus has to be configured, calibrated and fine-tuned for the intended use. For this purpose the said integrated controller may have an interface for communicating with external units selected from the group of computers, personal digital assistants and cellular telephones. This interface may be in the form of a wireless or wired connection between the integrated controller and the external unit, where the external unit uses a dedicated application for this purpose.

Additionally, the interface may be capable of transmitting information to external units, such as those mentioned earlier, in order to inform the individual being monitored of the current status of the apparatus or to transmit an alarm to the external unit.

It is well known within the art, that it is preferred to use a form of ultrasound transmission gel or similar means for coupling the ultrasonic transducers, such as the individual transducer arrays described in the present invention, to the body for increasing the transmission and reception efficiency of ultrasound signals to and from the body.

BRIEF DESCRIPTION OF THE DRAWINGS

The invention will now be explained more fully with reference to the drawings, in which:

FIG. 2 shows an example of the positions of seven individual transducer arrays for measuring the bladder volume, FIGS. 3.1, 3.2 show the arrangement of the individual transducer array from FIG. 2 in an enlarged section illustrating the structure of the individual transducer array in detail.

DETAILED DESCRIPTION OF THE PREFERRED EMBODIMENTS

Figure 1:
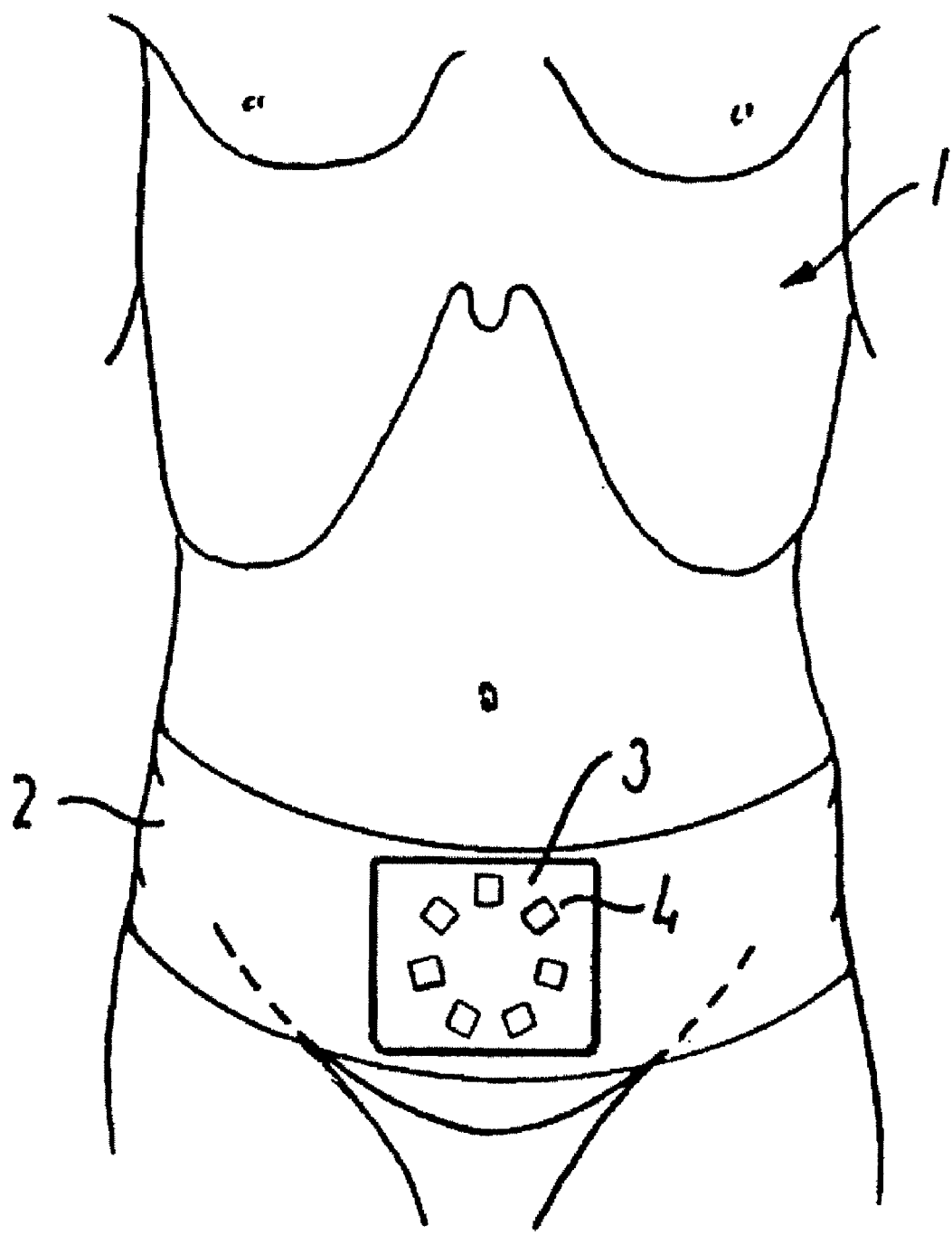
FIG. 1 shows the torso of an individual with an attached apparatus having a total of seven individual ultrasound transducer arrays for measuring the volume of the bladder.

FIG. 1 shows the torso of an individual 1 who is to have his bladder volume monitored.

With this end in view, the individual is provided with a fixture in the form of a belt 2, which may also be integrated in the waistband of the pants. The apparatus 3 for the bladder monitoring measurement is arranged in the belt, based on a plurality of individual ultrasound transducer arrays 4 that are of the phased-array type.

It is characteristic of the individual ultrasound transducer arrays that these can perform a scanning sweep in a plane without mechanical rotation of the individual transducer array, as the individual transducer array is composed of multiple piezoelectric crystals arranged in parallel which are capable of emitting signals in various angles by time delayed, individual excitation in a plane.

Figure 8:
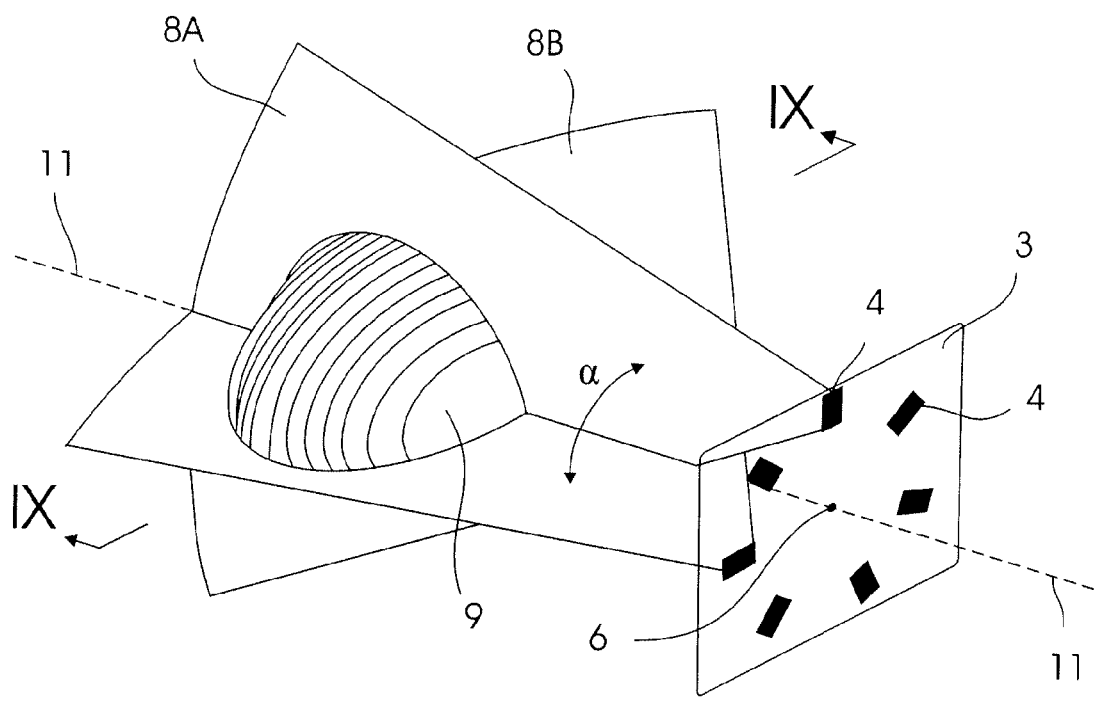
FIG. 8 shows a schematic diagram of the apparatus for monitoring the bladder volume, an urinary bladder, two scan planes transmitted by two out of seven individual transducer arrays of the apparatus and the axis.

The fixture, in which the apparatus is mounted, is positioned such that an axis (as shown in FIG. 8) which extends from a center point of the apparatus through the mass center of the bladder.

An enlarged section of the apparatus of FIG. 1 is shown in FIG. 2, where there are seven independent transducer arrays 4 which are positioned equidistantly on a closed curve, in this case a circle 5 having a center 6 which is intended to be positioned such that the said axis (not shown), positioned in the center 6, extends through the mass center of the bladder being measured. When at least three individual transducer arrays are used, it is optimal for the monitoring measurement that the individual transducer arrays are positioned equidistantly on the circle 5. This provides the best monitoring measurements of the bladder, as the scan planes from the individual transducer arrays are distributed as well as possible, thereby achieving the best distribution of input data FIG. 3.1 shows the positions of seven individual transducer arrays in a measurement setup, as shown in FIG. 2, and a section of an individual transducer array 4A is shown in an enlarged view in FIG. 3.2. The individual transducer arrays scan in a plane that extends away from the crystals in a direction which is perpendicular to the piezoelectric crystal beams 7. In FIG. 3.1, the transducer 4A will transmit a scan plane (not shown) which intersects the said axis (not shown) which extends from the center point 6 and the mass center of the bladder (not shown). Thus, it is a prerequisite for the optimum operation of the measurement setup that all the individual transducer arrays are oriented such that the scan plane is in parallel with a line drawn as the radius from the common center 6 to the center of the individual transducer array.

Figure 4:
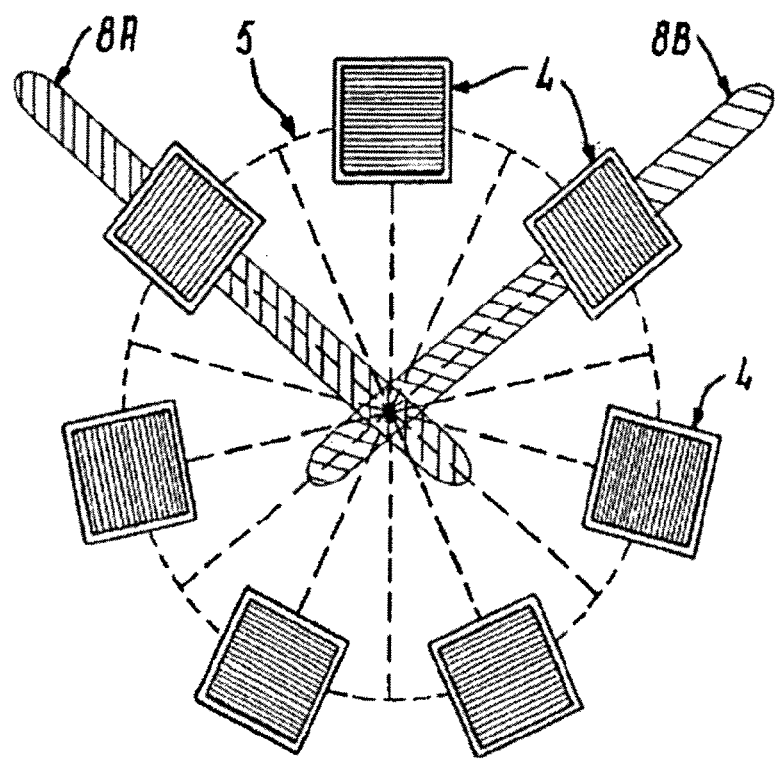
FIG. 4 shows two two-dimensional scan planes, viewed from a point on the said axis away from the abdominal surface, where the scan planes are transmitted from two arbitrary selected individual transducer arrays of a bladder volume monitoring apparatus that comprises seven individual transducer arrays.

FIG. 4 shows two scan planes 8A, 8B which are transmitted from two arbitrarily selected individual transducer arrays 4 from a bladder monitoring apparatus comprising seven individual transducer arrays. The scan planes 8A, 8B, from this viewpoint, follow the previously mentioned radius lines drawn such that they extend from a central point on the individual transducer arrays 4 to the common center 6.

Figure 5:
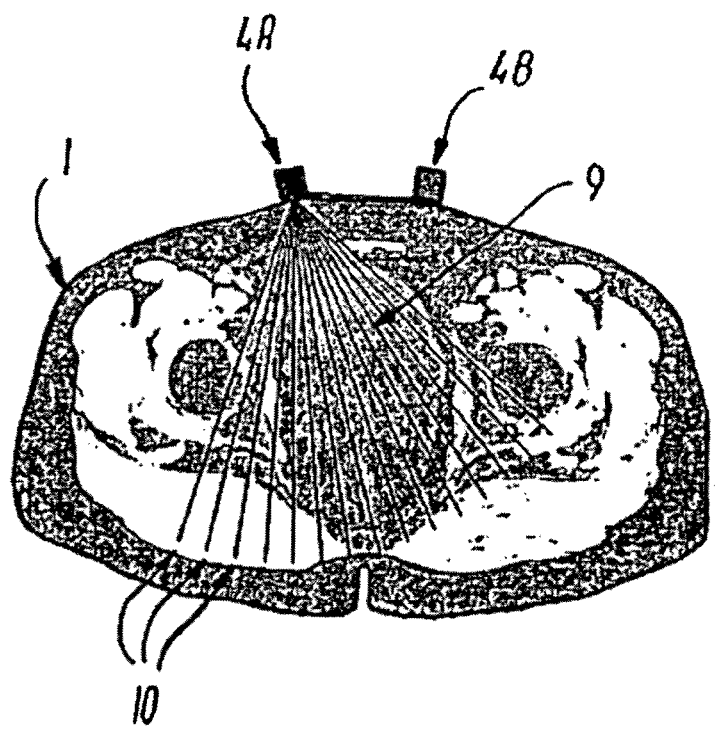
FIG. 5 shows a cross-sectional area of the body, viewed from the head and downwards, of an individual whose bladder volume is being monitored using individual transducer arrays. The figure shows radial lines of a scan plane in the body of the individual for one individual transducer array.

FIG. 5 shows a sectional area of the body 1, viewed from above, of an individual where the volume of the bladder 9 is to be monitored. The figure shows two individual transducer arrays 4A and 4B placed on the abdominal surface of the individual. Furthermore the figure shows radial scan lines 10 for the individual transducer array 4A, of a scan plane that is substantially in parallel to the body section.

Tests have shown that the best result of an ultrasound scanning of the bladder is achieved in the scan planes where the radial scan lines penetrate the surface of the bladder perpendicularly relative to it. Areas of the bladder that are substantially perpendicular to the travel direction of the ultrasound signal reflect the ultrasound signal optimally and produce the best information of the position of the bladder walls.

A perpendicular penetration of ultrasound signals relative to the surface of the bladder walls thus gives a better signal/noise ratio than monitoring measurements of bladder walls that are not perpendicular to the travel direction of the ultrasound signals.

Figure 6:
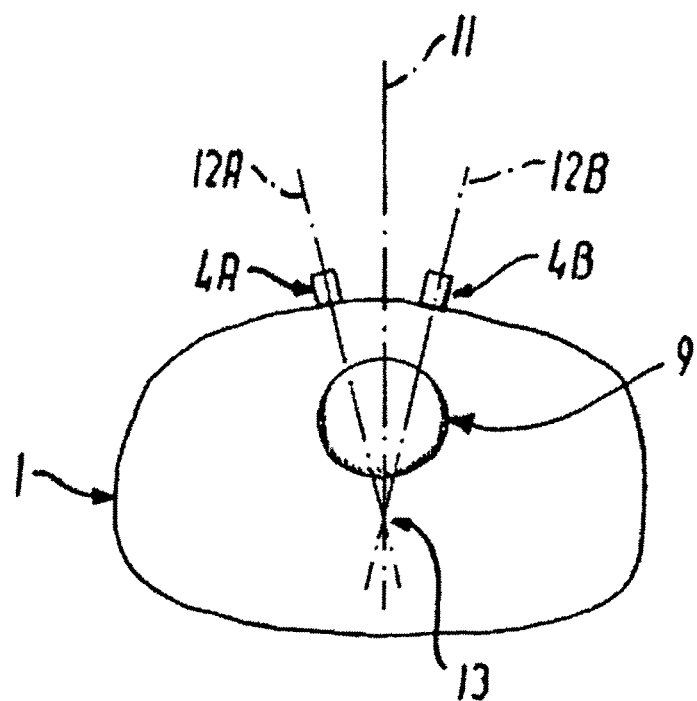
FIG. 6 shows a cross-sectional area of the body, viewed from the head and downwards, of an individual whose bladder volume is being monitored in accordance with a preferred embodiment of the present invention. The figure shows how two of the individual transducer arrays are directed toward the said axis within the body of the individual being measured.

The present invention enables continuous monitoring measurements based on other areas of the bladder than the front and back wall, and thereby to optimize the signal/noise ratio of monitoring measurements from different areas of the bladder. FIG. 6 shows a schematic diagram of the section presented in FIG. 5, where two individual transducer arrays 4A and 4B are arranged on the abdominal surface of the body 1 for the purpose of monitoring the volume of the bladder 9. As mentioned before, the individual transducer arrays are positioned on a closed curve, in this case a circle having a center through which an axis 11 is drawn, the at least two individual transducer arrays are positioned at a similar distance from the said axis at all points. To achieve the optimal position of the individual transducer arrays, the individual transducer arrays are positioned such that a surface normal of the transducer array face 12A and 12B, which extend from the individual transducer arrays, will intersect the axis 11 at a similar position 13 in a direction toward the bladder 9. The shown positioning of the individual transducer arrays ensures that each individual transducer array measures the bladder volume at an optimal angle, substantially in perpendicular relative to the bladder walls, which results in the positive influence on the signal/noise ratio of the ultrasound signal.

Figure 7:
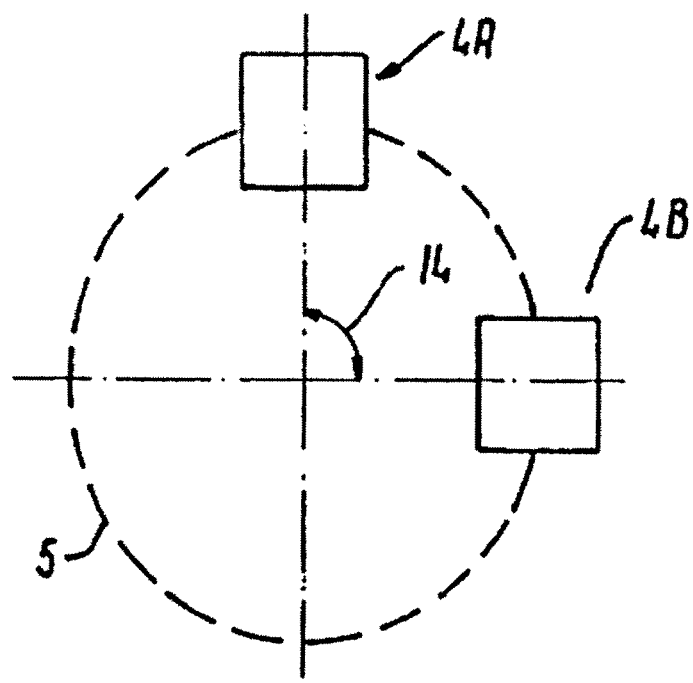
FIG. 7 shows the position of two individual transducer arrays according to a simple embodiment of the present invention, where two individual transducer arrays are used.

In the simple embodiment where two individual transducer arrays are used for monitoring the bladder volume, it is not optimal, however, to position the individual transducer arrays equidistantly on the closed curve 5. FIG. 7 shows the optimal position of two individual transducer arrays 4A and 4B which, as shown, are positioned such that the scan planes are at a 90 degree angle 14. This ensures that the scan planes may be related to their respective axes in a Cartesian system of coordinates corresponding to e.g. the X-axis and the Y-axis, the third axis being common to both scannings from which it is prior art to reconstruct a 3D representation of the object being measured.

FIG. 8 shows a schematical perspective view of an apparatus for monitoring the bladder volume 3, the bladder 9, two ultrasound scan planes 8A, 8B and the said axis 11, as seen in FIG. 4 and partially in FIG. 6. The apparatus 3 comprises seven individual transducer arrays 4, which are positioned along a closed curve (not shown) where the apparatus 3 is attached to the abdominal surface of the individual being monitored as shown in FIG. 1. The two scan planes 8A, 8B which are transmitted from two different independent transducer arrays 4 section the bladder 9 at different angles, with an angle α between the scan planes, which ensures that the ultrasound signal reflections come from different parts of the bladder 9. As the individual transducer arrays are positioned away from the axis 11 and the center point 6 of the apparatus, the radial lines (not shown) of the scan plane as shown in FIG. 5 originate at different positions, it is ensured that the monitoring measurements are based on reflections from bladder walls other than the front and back wall.

Figure 9:
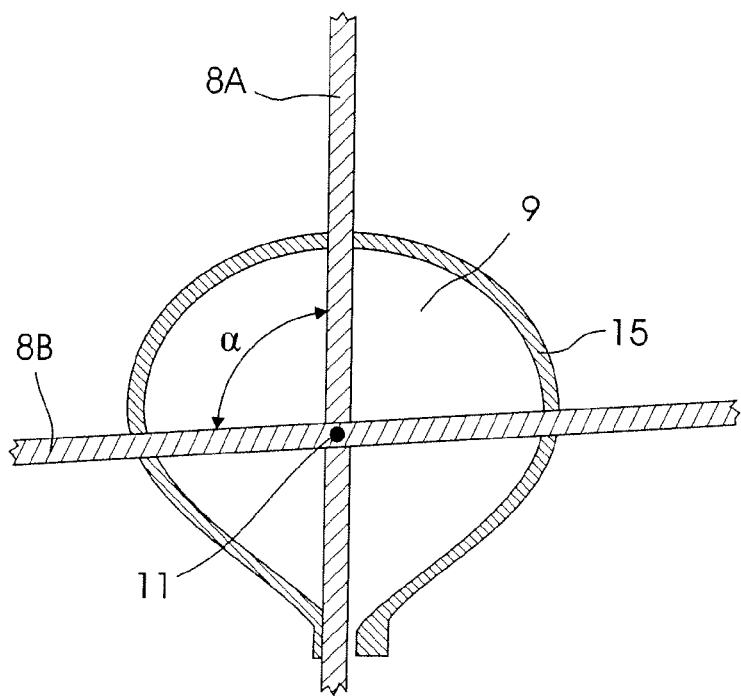
FIG. 9 shows a sectional diagram of the urinary bladder taken along the line IX-IX in FIG. 8, illustrating the angle between the two scan planes and the intersection of the axis of FIG. 8.

FIG. 9 shows a sectional area of the bladder 9, taken along the line IX-IX in FIG. 8. The ultrasonic scan planes 8A, 8B section the bladder at different angles, with an angle α between the scan planes, where the individual transducer arrays line up at eccentric positions away from the axis 11, which means, as earlier mentioned, that the monitoring measurements are based on different areas of the bladder wall 15.

The apparatus according to the present invention may advantageously comprise electronic circuits for controlling the individual transducer arrays, including excitation of these as well as data collection from the received signals. Electronic circuits in the form of signal processors or microprocessors will be capable of calculating the volume of the bladder on the basis of algorithms which are simple to develop for a person skilled in the art.

By connecting an external device to the apparatus through an wired or a wireless interface, where the external device is a computer, personal digital assistant or a mobile telephone, the apparatus may be pre-programmed, also to emit a signal when the volume of the bladder exceeds an optional level.

When the apparatus is connected wirelessly to external units, data may be exchanged between these, which allows remote-controlled programming of the apparatus and alarm to the external units.

Since the apparatus does not contain energy-intensive mechanical and electromechanical components, small and lightweight batteries may power the apparatus.

The described method and apparatus enables the continuous monitoring of the bladder volume in ambulatory or sleeping individuals.

The measurements are substantially without discomfort to the users because of the low weight and the small volume. Since the apparatus does not contain mechanical gears or electric motors, it is noise-free and sturdy as well as simple and inexpensive to manufacture.

What is claimed is:

1. A non-invasive method of monitoring the bladder volume in humans or animals, where the monitoring includes analysis of signals from a plurality of individual transducers including at least first and second individual ultrasound transducers, each transducer having an array comprising a plurality of transducer elements and a contact face, which arrays are arranged to transmit ultrasonic signals through an abdominal surface and to the bladder of an individual being monitored, wherein the method comprises arranging the transducers in spaced relation on the abdominal surface around and spaced from an axis which extends from a point on the abdominal surface to and through a point on or within the urinary bladder, wherein each transducer is arranged on the abdominal surface to scan the bladder using a scan plane which extends radially from the array to the bladder, wherein each of the transducers is arranged as a stand-alone array of ultrasound transducer elements combined into a single unit and so that the first transducer has a scan plane that intersects that of the second transducer; and further wherein the transducers are positioned away from the axis to emit and receive by reflection ultrasonic signals from the outer surface of the bladder so that the monitoring measurements define the outer surface of the bladder.

2. The method of claim 1, further comprising arranging the scan planes of the first and second transducers to intersect each other, and wherein a surface normal of the scan plane of the first transducer converges towards the scan plane of the second transducer.

3. The method of claim 1, further comprising arranging the point on or within the bladder to be positioned at the mass center of the bladder.

4. The method of claim 1, further comprising arranging each transducer array as an array of the phased-array kind.

5. The method of claim 1, further comprising arranging the at least first and second transducer arrays to operate one at a time.

6. The method of claim 1, further comprising arranging the at least first and second transducer arrays to be operated in a random order.

7. The method of claim 1, further comprising arranging the at least first and second transducer arrays to be operated sequentially along a path of a closed curve.

8. The method of claim 1, further comprising arranging the at least first and second transducer arrays to be fixed in place on a portable fixture which is attached to the individual being monitored.

9. The method of claim 8, further comprising arranging the portable fixture to be a strap, a belt, a girdle or a trouser waistband.

10. The method of claim 1, further comprising arranging the at least first and second transducer arrays to be fixed in place on the abdominal surface by an adhesive.

11. A non-invasive apparatus for monitoring the bladder volume in humans or animals, which comprises a plurality of individual transducers including at least first and second individual ultrasound transducer arrays, each transducer having an array comprising a plurality of transducer elements and a contact face, with each transducer being capable of an arranged placement on an abdominal surface of an individual being monitored in spaced relation around and spaced from an axis which extends from a point on the abdominal surface to and through a point on or within the urinary bladder, and means for scanning the bladder using a scan plane which extends radially from each transducer to the bladder, wherein each of the transducers is arranged as a stand-alone array of ultrasound transducer elements combined into a single unit and so that the first transducer has a scan plane that intersects that of the second transducer; and further wherein the transducers are positioned on the abdominal surface away from the axis to emit and receive by reflection ultrasonic signals from the outer surface of the bladder so that the monitoring measurements define the outer surface of the bladder.

12. The apparatus of claim 11, wherein the at least first and second transducer arrays are mounted such that each scan plane generated intersects each other, and wherein a surface normal of the scan plane of the first transducer converges towards the scan plane of the second transducer.

13. The apparatus of claim 11, wherein the at least first and second transducer arrays are of the phased-array kind.

14. The apparatus of claim 11, wherein the at least first and second transducer arrays are capable of being positioned on the abdominal surface around the axis at a 90° angle.

15. The apparatus of claim 11, further comprising at least three individual transducer arrays capable of being positioned on a closed curve upon the abdominal surface around the said axis in a pattern, wherein the closed curve is selected from the group consisting of a circle, an ellipse and an n-sided polygon.

16. The apparatus of claim 11, wherein the point on or within the bladder is the mass center of the bladder.

17. The apparatus of claim 11, wherein the at least first and second transducer arrays are configured to operate one at a time.

18. The apparatus of claim 15, wherein the at least-first and second transducer arrays are configured to operate sequentially along the path of the closed curve.

19. The apparatus of claim 11, wherein the at least first and second transducer arrays are configured to operate in a random order.

20. The apparatus of claim 11, further comprising a portable fixture that is capable of holding the at least first and second transducer arrays in place on the abdominal surface of the individual being monitored.

21. The apparatus of claim 20, wherein the portable fixture is selected from the group consisting of a waist strap, a belt, a girdle and a trouser waistband.

22. The apparatus of claim 11, wherein the at least first and second transducer arrays are intended to be held in place on the abdominal surface of the individual being monitored using an adhesive.

23. The apparatus of claim 20, wherein the portable fixture has an integrated controller, which has electronic circuits, at least one microprocessor, memory storage and means for controlling the ultrasound signal transmission and reception of the at least-first and second transducer arrays, processing the ultrasound signals received by the at least-first and second transducer arrays, registering the monitoring measurements and providing alarming means for alarming the individual being monitored.

24. The apparatus of claim 23, wherein the integrated controller has an interface for communicating with external units selected from the group consisting of computers, personal digital assistants and cellular telephones.

25. The apparatus of claim 11, further comprising a battery, wherein the apparatus is battery operated.

26. The apparatus of claim 11, wherein the two individual transducers are arranged in such a way that two scan planes produced by the transducers are not parallel to each other, and intersect each other in the axis.

27. The apparatus of claim 11, wherein a surface normal of each transducer contact face is arranged to converge towards the axis.

28. The apparatus of claim 11, wherein the transducers are one-dimensional transducers.

* * * * *

UNITED STATES PATENT AND TRADEMARK OFFICE
CERTIFICATE OF CORRECTION

PATENT NO.        : 8,398,553 B2                                    Page 1 of 1
APPLICATION NO.   : 11/621748
DATED             : March 19, 2013
INVENTOR(S)       : Kristiansen It is certified that error appears in the above-identified patent and that said Letters Patent is hereby corrected as shown below:

Title Page:
Insert the foreign application priority data as follows:

Item -- (30)   Foreign Application Priority Data
        May 19, 2001   (DK) .................. 2001 00807
        Nov. 20, 2001  (DK) .................. 2001 01728 --.

In the Claims:
Column 14:
Line 11 (claim 18, line 1), change "least-first" to -- least first --.
Line 32 (claim 23, line 5), change "least-first" to -- least first --.
Line 33 (claim 23, line 6), change "least-first" to -- least first --.

Signed and Sealed this
Twenty-eighth Day of May, 2013

Teresa Stanek Rea
*Acting Director of the United States Patent and Trademark Office*